US010412985B2

(12) United States Patent
Byron et al.

(10) Patent No.: US 10,412,985 B2
(45) Date of Patent: Sep. 17, 2019

(54) IDENTIFYING COMPONENTS BASED ON OBSERVED OLFACTORY CHARACTERISTICS

(71) Applicant: International Business Machines Corporation, Armonk, NY (US)

(72) Inventors: Donna K. Byron, Petersham, MA (US); Carmine Michael Dimascio, West Roxbury, MA (US); Florian Pinel, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 280 days.

(21) Appl. No.: 15/280,843

(22) Filed: Sep. 29, 2016

(65) Prior Publication Data

US 2018/0084809 A1 Mar. 29, 2018

(51) Int. Cl.
*G01N 33/02* (2006.01)
*A23L 27/00* (2016.01)
(Continued)

(52) U.S. Cl.
CPC ............... *A23L 27/00* (2016.08); *A23L 27/10* (2016.08); *A23L 27/88* (2016.08); *G01N 30/72* (2013.01);
(Continued)

(58) Field of Classification Search
CPC ......... A23L 27/00; A23L 27/88; G01N 30/72; G01N 33/0001; G01N 30/7206; G01N 33/02–33/146; G01N 2033/4975
(Continued)

(56) References Cited

U.S. PATENT DOCUMENTS 4,914,277 A * 4/1990 Guerin .................... F24C 7/087
219/492
5,177,995 A * 1/1993 Risch ....................... G01N 1/44
73/23.41
(Continued)

FOREIGN PATENT DOCUMENTS

CN 101603959 A 12/2009
IN 3032/CHE/2011 A 6/2013

OTHER PUBLICATIONS

Somboon et al., "Development of Odor Recorder with Enhanced Recording Capabilities Based on Real-Time Mass Spectrometry," Sensors and Actuators B 141 (2009) 141-146, Elsevier, 2009.
(Continued)

*Primary Examiner* — Drew E Becker
(74) *Attorney, Agent, or Firm* — Patterson + Sheridan, LLP

(57) ABSTRACT

Techniques are disclosed for providing suggestions based on a flavor signature delta measured between samples prepared according to a recipe. An application obtains a flavor signature for a canonical sample prepared according to the recipe and a flavor signature for a sample subsequently prepared according to the recipe. The application generates a flavor signature delta from the flavor signatures of the samples. The flavor signature delta indicates a difference in the measure of each of the olfactory compounds in the samples. The application identifies one or more ingredients, each ingredient identified from at least one of the olfactory compounds present in the flavor signature delta. The application then generates one or more suggestions for preparing a sample based on the identified ingredients.

20 Claims, 8 Drawing Sheets

(51) Int. Cl.
　　　*G01N 33/00*　　　　(2006.01)
　　　*G01N 30/72*　　　　(2006.01)
　　　*A23L 27/10*　　　　(2016.01)
　　　*G01N 33/497*　　　(2006.01)

(52) U.S. Cl.
　　　CPC ......... *G01N 33/0001* (2013.01); *G01N 33/02* (2013.01); *A23V 2002/00* (2013.01); *G01N 30/7206* (2013.01); *G01N 2033/4975* (2013.01)

(58) Field of Classification Search
　　　USPC ........... 73/23.34–23.42, 865.7; 426/231–233
　　　See application file for complete search history.

(56) References Cited

U.S. PATENT DOCUMENTS

| | | | | |
|---|---|---|---|---|
| 6,066,347 | A * | 5/2000 | Prasad | B65D 81/3446 426/107 |
| 6,294,209 | B1 * | 9/2001 | Andersson | B65D 81/3294 426/115 |
| 6,450,008 | B1 * | 9/2002 | Sunshine | B82Y 15/00 702/27 |
| 6,486,453 | B1 * | 11/2002 | Bales | H05B 6/6435 219/400 |
| 6,541,052 | B1 * | 4/2003 | Rohleder | G09F 3/02 426/132 |
| H2215 | H | 4/2008 | Allen et al. | |
| 7,559,225 | B2 * | 7/2009 | Davidson | G09B 23/28 73/23.3 |
| 7,565,273 | B2 * | 7/2009 | Hengerer | G01N 33/02 116/214 |
| 9,519,620 | B1 * | 12/2016 | Pinel | G06F 16/34 |
| 9,870,550 | B2 * | 1/2018 | Byron | G06Q 10/087 |
| 2001/0026822 | A1 * | 10/2001 | Lee | A23L 5/15 426/241 |
| 2001/0027355 | A1 * | 10/2001 | Lee | F24C 7/08 700/211 |
| 2002/0076473 | A1 * | 6/2002 | Reinders | A23C 9/1307 426/534 |
| 2005/0048186 | A1 * | 3/2005 | Lehmberg | A23F 3/38 426/594 |
| 2005/0178185 | A1 * | 8/2005 | Negri | G01N 33/0031 73/23.34 |
| 2005/0287286 | A1 * | 12/2005 | Gaonkar | A23P 10/35 426/651 |
| 2007/0191257 | A1 * | 8/2007 | Andretta | A61Q 13/00 512/1 |
| 2008/0193614 | A1 * | 8/2008 | Greiner | F24C 7/08 426/231 |
| 2008/0264269 | A1 * | 10/2008 | Sterzel | F24C 7/08 99/331 |
| 2009/0110590 | A1 * | 4/2009 | Sim | A61L 9/00 422/4 |
| 2010/0292998 | A1 * | 11/2010 | Bodlaender | G06Q 30/0603 705/2 |
| 2013/0040025 | A1 * | 2/2013 | Morganti | A23B 4/044 426/312 |
| 2013/0149675 | A1 * | 6/2013 | Slone | G09B 19/00 434/127 |
| 2013/0171304 | A1 * | 7/2013 | Huntley | G06Q 50/00 426/231 |
| 2014/0295822 | A1 * | 10/2014 | Koo | G06Q 20/3278 455/420 |
| 2015/0059438 | A1 * | 3/2015 | Varshney | G01N 33/0001 73/23.34 |
| 2015/0149120 | A1 | 5/2015 | Burkhardt et al. | |
| 2015/0157752 | A1 * | 6/2015 | Varshney | G06F 16/9024 424/76.1 |
| 2015/0199608 | A1 * | 7/2015 | Pinel | G06Q 10/067 706/46 |
| 2015/0205998 | A1 * | 7/2015 | Suh | G06K 9/00281 382/118 |
| 2015/0276700 | A1 * | 10/2015 | Goel | G01N 33/02 73/865.7 |
| 2015/0290795 | A1 | 10/2015 | Oleynik | |
| 2015/0346176 | A1 * | 12/2015 | Hort | G01N 33/02 73/23.34 |
| 2016/0066744 | A1 | 3/2016 | Baxi et al. | |
| 2016/0372005 | A1 * | 12/2016 | Bajpai | G09B 19/0092 |
| 2017/0011164 | A1 * | 1/2017 | Adoni | G06N 5/04 |
| 2017/0027385 | A1 * | 2/2017 | Tassan Mangina | H05B 1/0261 |
| 2017/0139902 | A1 * | 5/2017 | Byron | G06Q 10/087 |
| 2017/0193096 | A1 * | 7/2017 | Bhatt | G06F 17/30699 |
| 2017/0235734 | A1 * | 8/2017 | Byron | G06F 17/3053 707/740 |
| 2018/0088095 | A1 * | 3/2018 | Byron | G01N 33/0001 |

OTHER PUBLICATIONS

Somboon et al., "Development of Odor Recorder for Practical Odor Recording Application," Advances in Sensors, Signals and Materials (WSEAS), pp. 89-93, 2010.

Dymerski et al., "An Odor-Sensing System—Powerful Technique for Foodstuff Studies," Review of Scientific Instruments 82, pp. 1-32, Nov. 2011.

Hodgins et al., "The Electronic NOSE and its Application to the Manufacture of Food Products," J of Automatic Chemistry, v.17, n.5 (Sep.-Oct. 1995), pp. 179-185, Taylor & Francis Ltd., 1995.

* cited by examiner

US 10,412,985 B2

IDENTIFYING COMPONENTS BASED ON OBSERVED OLFACTORY CHARACTERISTICS

BACKGROUND

The present disclosure relates to food preparation, and more specifically, to providing suggestions for a prepared dish based on olfactory characteristics observed in a canonical version and an actual version of the dish.

Devices for sensing or diffusing smells have a number of applications in the culinary community. For example, as gas chromatography-mass spectrometry (GC-MS) devices become more portable, a cook can capture odor compounds of various ingredients used in recipes. The cook may then analyze the odor compounds of the ingredients to further develop recipes, e.g., where each ingredient complements the other based on the odor compounds. As another example, portable odor diffusing devices provide convenience for users to reproduce certain odors based on a given odor compound. For instance, the odor diffusing device can allow a user to accurately simulate the scent of a certain ingredient without the ingredient actually being physically present.

Indeed, the prominence of odor sensing and diffusing devices may address certain issues with a dining experience. One particular issue is where a dish does not meet expectations of a diner because of the taste or the smell of the dish. This can happen for a variety of reasons. For example, although a dish may have been prepared according to a recipe, the dish nevertheless may have been prepared by a less skilled cook. As another example, a cook may have substituted ingredients described in a recipe for lower quality ingredients (e.g., due to monetary constraints or the originally described ingredients being unavailable in a current season).

Further, failure to meet expectations is also subjective and may depend on a diner. For instance, ingredient substitutions may be necessary to accommodate allergies or other dietary constraints of a diner. In addition, diners may have different sensibility thresholds to different flavors, e.g., a given diner may think a recipe does not have enough of a certain spice where another diner eating the identical dish thinks the amount of spice is appropriate. Therefore, personalizing a dish for a diner presents challenges.

SUMMARY

One embodiment presented herein discloses a method. The method generally includes obtaining a first flavor signature for a first sample and at least a second flavor signature for a second sample. The first and second flavor signatures each provide a measure indicating a presence for each of a plurality of olfactory compounds in the first and second samples, respectively. A flavor signature delta is generated from the first and second flavor signatures. The flavor signature delta indicates a difference in the measure of each of the olfactory compounds in the first sample and the measure of each of the olfactory compounds in the second sample. One or more ingredients not present in the second sample are identified. Each food ingredient is identified from at least one of a plurality of olfactory compounds present in the flavor signature delta. One or more suggestions for preparing a third sample are generated based on the identified ingredients and the second sample.

Another embodiment presented herein discloses a computer program product including a computer-readable storage medium storing instructions. The instructions, when executed by a processor, perform an operation. The operation itself generally includes obtaining a first flavor signature for a first sample and at least a second flavor signature for a second sample. The first and second flavor signatures each provide a measure indicating a presence for each of a plurality of olfactory compounds in the first and second samples, respectively. A flavor signature delta is generated from the first and second flavor signatures. The flavor signature delta indicates a difference in the measure of each of the olfactory compounds in the first sample and the measure of each of the olfactory compounds in the second sample. One or more ingredients not present in the second sample are identified. Each food ingredient is identified from at least one of a plurality of olfactory compounds present in the flavor signature delta. One or more suggestions for preparing a third sample are generated based on the identified ingredients and the second sample.

Yet another embodiment presented herein discloses a system having a processor and a memory. The memory stores program code, which, when executed on the processor, performs an operation. The operation itself generally includes obtaining a first flavor signature for a first sample and at least a second flavor signature for a second sample. The first and second flavor signatures each provide a measure indicating a presence for each of a plurality of olfactory compounds in the first and second samples, respectively. A flavor signature delta is generated from the first and second flavor signatures. The flavor signature delta indicates a difference in the measure of each of the olfactory compounds in the first sample and the measure of each of the olfactory compounds in the second sample. One or more ingredients not present in the second sample are identified. Each ingredient is identified from at least one of a plurality of olfactory compounds present in the flavor signature delta. One or more suggestions for preparing a third sample are generated based on the identified ingredients and the second sample.

DETAILED DESCRIPTION

Figure 1:
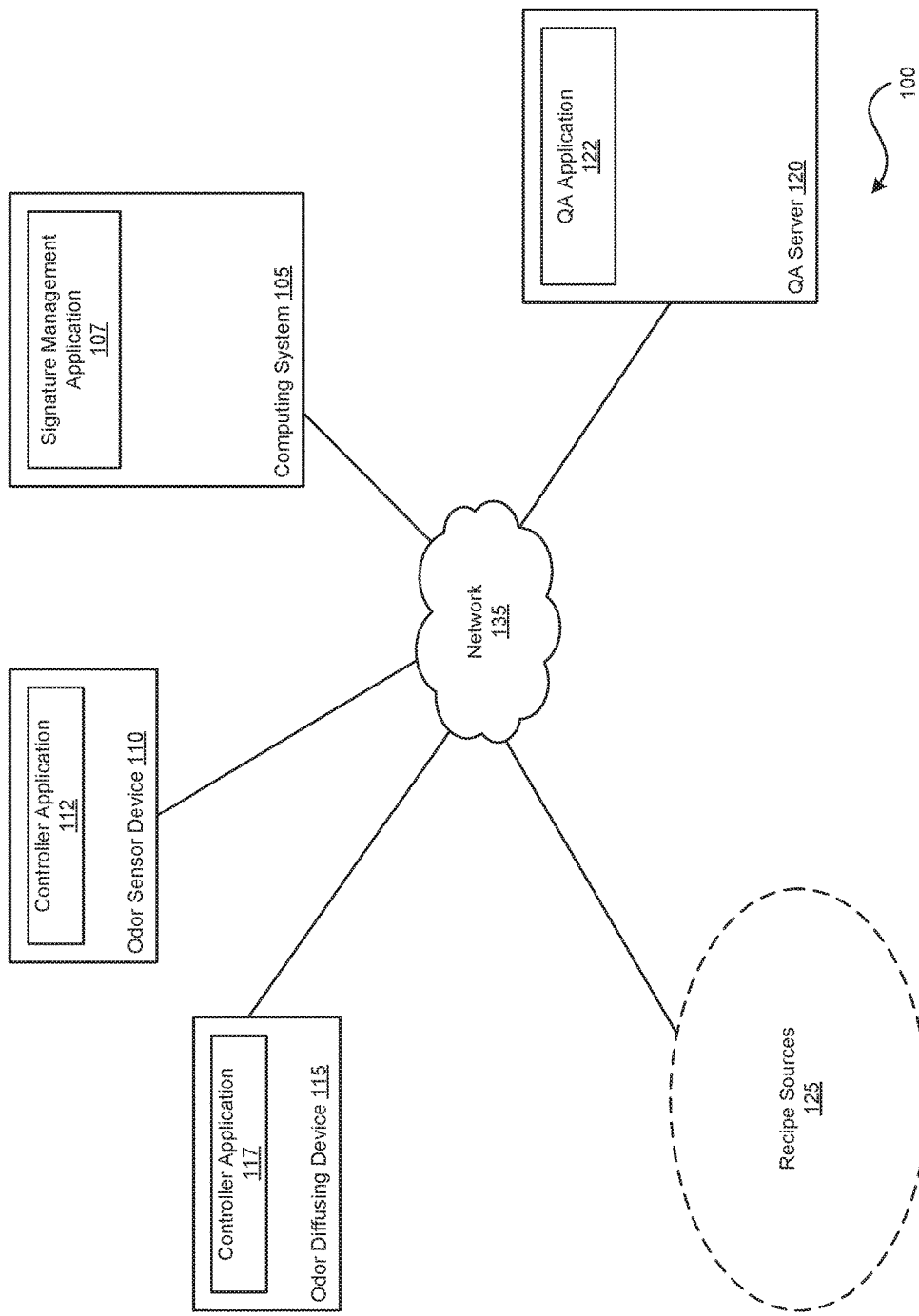
FIG. 1 illustrates an example computing environment, according to one embodiment.

Embodiments presented herein disclose techniques for sensing and adjusting olfactory characteristics (also referred to herein as odor characteristics) of a dish (i.e., a sample of a dish) based on flavor signature data obtained during or after the preparation of the dish. In one embodiment, an olfactory sensor device (also referred to herein as an odor sensor device) obtains a flavor signature of a dish prepared according to a canonical standard. For example, the dish may have been prepared by a chef who authored a recipe for preparing the dish. The flavor signature may include a number of volatile flavor compounds indicating ingredients present in the dish. A computing system may store this canonical flavor signature for subsequent use. In one embodiment, the computing system is also configured to maintain diner profiles, where a given profile provides information regarding dietary constraints (e.g., allergies, dislikes, etc.), flavor biases (e.g., sensitivities to a given ingredient), and flavor memories (e.g., experiences with a given dish) for a diner.

In one embodiment, the odor sensor device obtains an actual flavor signature of a dish prepared subsequent to the canonical dish. For example, the dish may have been prepared at a restaurant as an order for a diner and subject to dietary constraints of the diner. As will be further described below, the computing system may then retrieve the actual flavor signature from the odor sensor device and generate a flavor signature delta from the canonical flavor signature and the actual flavor signature. The computing system may evaluate the flavor signature delta to identify differences between the actual dish and the prepared dish (i.e., between the sample previously analyzed, and the newly prepared sample). For example, the flavor signature delta may include certain compounds representative of an ingredient present in the canonical dish that is absent from the actual dish.

The computing system may use the flavor signature delta for a variety of applications. For example, the computing system may identify, from the flavor signature delta, olfactory or aromatic compounds (also referred to herein as odor compounds) corresponding to odor characteristics that are absent from the actual dish but present in the canonical dish. For example, assume that a pizza canonically prepared by a chef includes odors corresponding to the presence of garlic. Further, assume that the dish, as actually prepared, lacks such odors. The flavor signature of the canonical dish and the flavor signature of the actual dish may result in a flavor signature delta that indicates that the odor compound representing garlic is absent in the actual dish. Consequently, the computing system can identify that garlic is missing from the actual dish.

As will be further described below, in one embodiment, the computing system may direct an aroma diffusing device (also referred to herein as an odor diffusing device) to generate a personalized odor mixture based on the odor compounds identified in the flavor signature delta. For example, the computing system may determine a mapping of the data reflected in the flavor signature delta to odor compounds that may be emitted by the odor diffusing device. The computing system may then, e.g., via an underlying application programming interface (API) for the odor diffusing device, send a request to the odor diffusing device containing that mapped odor compounds to emit. In turn, the odor diffusing device may generate and emit the odors, e.g., to complement the odors emitting from the actual dish.

Advantageously, generating an odor mixture from odor compounds identified in a flavor signature delta improves a diner experience by complementing a dish with odors that are ordinarily present (e.g., with a canonical dish) but are not present with a dish that is actually prepared by a user. Further, the computing system may also adjust the flavor signature delta based on a profile associated with a diner, which indicates dietary constraints and the like that the diner may have. For example, for a pizza recipe, if a cook substitutes pizza dough for a cauliflower crust to account for dietary constraints of a diner that restrict carbohydrate intake, the resulting flavor signature delta may indicate that an odor corresponding to a baked bread pizza crust is missing (and the smell of the resulting pizza may not be as satisfying to the diner). However, a generated odor mixture including an odor corresponding to the smell of baked bread pizza crust can compensate for the absence of that smell in the dish—thus providing an improved experience for the diner.

Further, in some cases, a user (e.g., a chef, cookbook author, etc.) may obtain a flavor signature for a canonical dish at certain stages of preparation of the dish. Doing so allows another user (e.g., a cook subsequently preparing the dish) to also obtain flavor signatures at each stage to generate flavor signature deltas corresponding to each stage. In one embodiment, the computing system may identify, based on a given flavor signature delta, missing ingredients or cooking techniques that should have been applied in the corresponding stage. The computing system may also generate, from the identified missing ingredients and cooking techniques, one or more suggestions to present to the user, e.g., for later preparation stages or for future preparation of the dish. For example, to do so, the computing system may query a question answering (QA) service configured to analyze recipes based on ingredients provided as part of the query. In turn, the QA service may determine one or more combinations of ingredients or cooking techniques to include at certain stages of preparation of the dish. Once received, the computing system may present the combinations to a user interface for the user to review.

Advantageously, providing suggestions to a user (e.g., a cook preparing a dish according to a recipe associated with one or more canonical flavor signatures) based on a flavor signature delta obtained at various stages of preparation of the dish allows the user to prepare a dish according to a recipe with greater accuracy. For example, if, at a given stage of preparation of a dish, a flavor signature delta indicates a large deviation between the canonical flavor signature and the actual flavor signature, the computing system may generate ingredient or technique suggestions for compensating for the flavor signature delta (or generate such suggestions for another attempt at preparing the dish), each suggestion generated based on combinations of ingredients identified as missing or inadequate in the flavor signature delta. Further advantageously, the suggestions may provide additional training for a user in preparing the dish.

FIG. 1 illustrates an example computing environment 100, according to one embodiment. As shown, the computing environment 100 includes a computing system 105, an odor sensor device 110, an odor diffusing device 115, a question answering (QA) server 120, one or more recipe sources 125, and one or more dietary constraint sources 130, each interconnected via a network 135 (e.g., the Internet).

In one embodiment, the computing system 105 includes a signature management application 107. Further, in one embodiment, the computing system 105 may be a physical computing system or a virtual computing instance executing in the cloud. The computing system 105 may interconnect with the odor sensor device 110 and the odor diffusing device 115 wirelessly (or via a wired connection, e.g., via a USB connector). In one embodiment, the odor sensor device 110 is configured to capture odors from a given sample. The odor sensor device 110 may use various techniques, such as gas chromatography and mass spectrometry, to analyze odor compounds. For example, given a sample of a dish prepared according to a recipe, a controller application 112 executing on the device may cause the odor sensor device 110 to volatilize the sample and carry, by an inert gas, the sample to a detector. The controller application 112 may cause the detector to obtain a spectrum of fragmented compounds. The controller application 112 may then generate quantitative measurements corresponding to odor compounds of the dish.

In one embodiment, the signature management application 107 obtains the odor compounds from the odor sensor device 110. For example, the signature management application 107 may transmit a request to the controller application 112 (e.g., via an application programming interface (API) that allows communication with the controller application 112) for the odor compounds. Once received, the signature management application 107 may generate a flavor signature from the odor compounds. In one embodiment, a flavor signature may be represented as a sparse vector, where a positive non-zero value at an index indicates the presence of a given odor compound and a zero value indicates a lack of a compound for that index. Of course, one of skill in the art will recognize that the flavor signature can be represented as other types of data structures used to contain information describing an odor compound (e.g., a vector, key-value pair, etc.)

In one embodiment, the odor diffusing device 115 is a portable device configured with a variety of base scent cartridges that provides a palette for creating numerous types of odors. The odor diffusing device 115 may, via a controller application 117, generate and emit an odor mixture based on combinations of the scent cartridges. Further, the odor diffusing device 115 may be configured with smartphone capabilities, such as voice dialing, messaging, data transfer, and the like. For instance, the odor diffusing device 115 may receive messages having a given odor mixture encoded therein. Further, the signature management application 107 may send a request the controller application 117 (e.g., via an API allowing third-party applications to access functionality of the odor diffusing device 115) to emit an odor mixture directly.

In one embodiment, the signature management application 107 is configured to obtain a flavor signature for a food dish. As stated, the signature management application 107 communicates with the odor sensor device 110 (through the controller application 112) to obtain data corresponding to odor compounds taken from a sample of the food dish. The signature management application 107 may then normalize the data to a sparse vector representing the flavor signature.

Further, the signature management application 107 may determine differences between a flavor signature of two versions of a given dish. For example, a user, such as a chef or a cookbook author, may create a recipe and prepare a dish according to that recipe (referred to herein as a "canonical dish"). The user may capture odor compounds of the dish, e.g., using the odor sensor device 110. The signature management application 107 may then obtain the odor compounds from the odor sensor device 110 and create a flavor signature for the dish. Further, the signature management application 107 may associate the flavor signature with a recipe profile corresponding to the dish and store the recipe profile containing the flavor signature in a data store.

Subsequently, another user, such as a cook, may prepare a dish according to the recipe (referred to herein as an "actual dish"). The user may capture odor compounds of the dish, e.g., using an odor sensor device 110. The signature management application 107 may then obtain the odor compounds from the odor sensor device 110 and create a flavor signature for the actual dish. Further, the signature management application 107 may generate, based on a difference of the flavor signature of the canonical dish and the flavor signature of the actual dish, a flavor signature delta.

In one embodiment, the flavor signature delta is a sparse vector representing the difference between the flavor signatures. In particular, an index in the flavor signature delta that has a non-zero value indicates that a corresponding odor compound is present in the canonical dish but absent (or are relatively weak compared to the canonical dish flavor signature) in the actual dish. Negative values present in an initial calculation of the flavor signature delta may indicate odor compounds present in the actual dish but absent in the canonical dish. Generally, such odor compounds cannot be removed from the actual dish, so in one embodiment, the signature management application 107 may, in the flavor signature delta, set an index having a negative value to zero.

In one embodiment, the signature management application 107 may use the flavor signature delta for determining a mixture of odor compounds to account for missing or inadequate odors of a dish that would otherwise be present in a canonical version of a dish (or desired by a diner based on dietary preferences). As further described below, the signature management application 107 may direct the odor diffusing device 115 to generate the mixture of odor compounds identified in the flavor signature delta. As a result, the odor diffusing device 115 may diffuse the odors, consequently complementing the odors emanating from the actual dish.

In one embodiment, the signature management application 107 may use the flavor signature delta to identify ingredients missing from a dish that would otherwise be present in a canonical version of a dish). As further described below, the signature management application 107 may generate suggestions for ingredients to add (e.g., "Add more basil") or cooking techniques to perform (e.g., "Brown the meat further") based on the missing odor compounds identified in the flavor signature delta. For example, the signature management application 107 may identify mappings from a given odor compound (or set of odor compounds) to an amount of a particular ingredient or a given cooking technique that results in the odor compound becoming present.

In some cases, the signature management application 107 may identify more than one ingredient corresponding to a particular compound. In such a case, the signature management application 107 may generate a query to be readable by a QA application 122 executing on the QA server 120. Generally, the QA application 117 provides a cognitive web service that analyzes a variety of recipe sources 125 (e.g., cookbooks, recipe databases, online recipe websites, and the like) to learn food pairing theories and complex relationships between various flavor compounds. The query sent by the signature management application 107 may include a recipe, dish name, and the identified ingredients. In turn, the QA application 122 may return a listing of recipe combinations using the identified ingredients. The signature management application 107 may output, to the user, the listing of combinations as ranked (e.g., by number of similar recipes using the ingredients, relevance, and the like).

Figure 2:
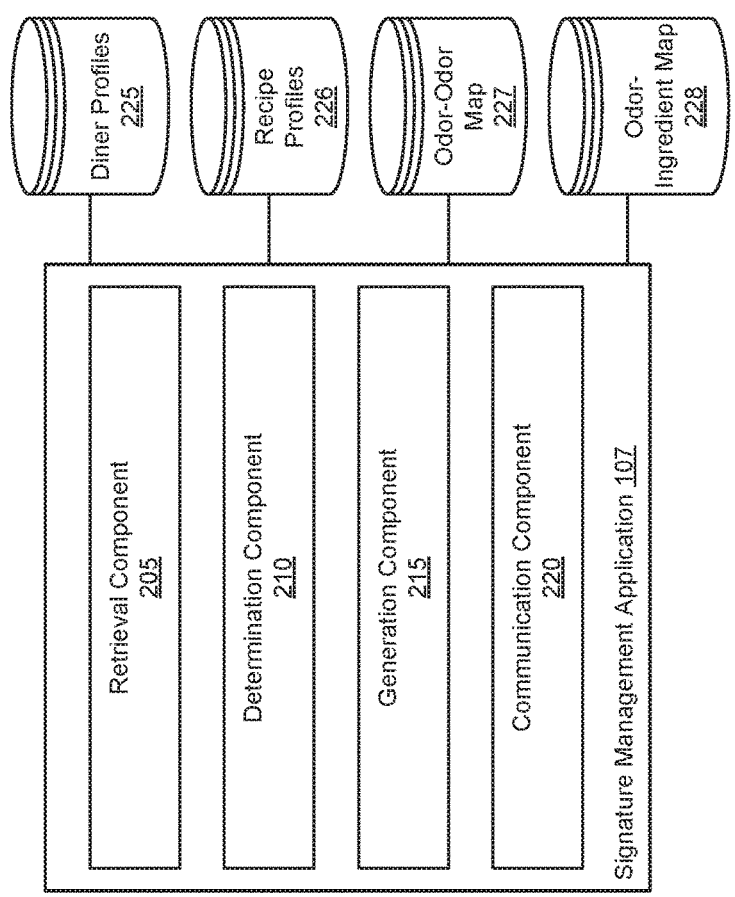
FIG. 2 further illustrates the signature management application described relative to FIG. 1, according to one embodiment.

FIG. 2 further illustrates the signature management application 107 described relative to FIG. 1, according to one embodiment. As shown, the signature management application 107 includes a retrieval component 205, a determination component 210, a generation component 215, a communication component 220, one or more diner profiles 225, one or more recipe profiles 226, an odor-odor map 227, and odor-ingredient map 228.

The signature management application 107 may maintain the diner profiles 225 in a data store, e.g., in the cloud, via a database service, or in a local store. In one embodiment, a diner profile 225 specifies dietary constraints, flavor biases, and flavor memories corresponding to a particular diner consuming a dish. For example, specified dietary constraints can include allergy information, caloric intake restrictions, macronutrient intake restrictions, and the like. Flavor biases specify diner reactions and sensitivities towards a particular ingredient for a given dish, e.g., whether garlic flavor was strong with the dish, or whether the dish needed more salt, etc. Further, flavor memories may include descriptions of a given dish made by the diner (e.g., the smell of smoke of barbecue).

The information associated with the diner profile 225 may be specified by the diner or obtained using diner information, such as account information provided by the diner to restaurant review websites, fitness tracker applications, and the like. For example, flavor memories for a diner can be retrieved using natural language processing (NLP) techniques on reviews written by a diner. Such techniques may use learning models to determine aromatic terms used to describe a dish or components of the dish (e.g., "smokiness" when describing a barbeque dish, "citrus" when describing a dessert, etc.). Similarly, flavor biases for a given dish may be submitted by a diner in a feedback form provided by a user.

Further, the signature management application 107 may maintain one or more recipe profiles 226, each recipe profile 226 corresponding to a given dish. The recipe profile 226 may include a recipe (e.g., authored by a chef, or included as part of a cookbook), annotations for the recipe, tag metadata for the recipe (e.g., describing dish type, whether the recipe includes meat, is gluten-free, etc.), and the like. Further, the recipe profile 226 may include one or more flavor signatures representing a canonical version of the underlying dish. For example, a flavor signature may be captured at various stages of preparing the dish (e.g., initial preparation, after the inclusion of an ingredient, shortly after taking the dish out of the oven, etc.). In other cases, a single flavor signature may be associated with the recipe profile 226 representing the dish after preparation of the dish is complete.

The retrieval component 205 is configured to obtain measurements corresponding to odor compounds from the odor sensor device 110. For example, the measurements correspond to odor compounds observed in a sample of a dish prepared according to a recipe, such as a recipe associated with a given recipe profile 226. Once captured, the retrieval component 205 may convert the measurements to a sparse vector representing a flavor signature. Further, the retrieval component 205 may receive an indication, e.g., by a user, that the odor compounds are associated with a particular recipe profile 226. Further still, the indication may also include a stage of preparation with which to associate the measurements. In some cases, such as if the flavor signature corresponds to that of a dish being prepared for a diner, the retrieval component 205 may also obtain a diner profile 225 associated with that diner.

The determination component 210 is configured to evaluate one or more flavor signatures, e.g., corresponding to that of a canonical dish and of an actual dish. The determination component 210 does so to identify differences in odor compounds between the flavor signatures. For example, to do so, the determination component 210 may subtract the underlying sparse vector of the flavor signature of the actual dish from the sparse vector of the flavor signature of the canonical dish. In one embodiment, the determination component 215 creates a flavor signature delta from the results. Once generated, the determination component 210 may then store the flavor signature delta in a data store and associate the flavor signature delta with the recipe profile 226.

In addition, the determination component 210 may adjust values in the flavor signature delta based on a diner profile 225. For example, if the diner associates a given dish with the smell of smoke, the determination component 210 may increase the value in the index associated with the odor compound of smoke by a predefined amount. As another example, if the diner has a lower sensibility to a given herb or spice present in the actual dish, the determination component 210 may increase the values of the index corresponding to the odor compounds contained in that herb or spice.

In one embodiment, the generation component 215 may identify mappings of odor compounds specified in a given flavor signature delta to odor compounds that can be emitted from the odor diffusing device 115. For example, the odor-odor map 227 provides such mappings for translating the flavor signature delta to a mixture of odor compounds that use the available cartridges of the diffuser. The mappings themselves may be predefined, such as by a manufacturer. The mappings may also be predefined based on a training set of flavor vectors—under this approach, a machine learning algorithm (e.g., feature extraction, dimension reduction, etc.) can be used to learn flavor combinations that can be mixed to reproduced the flavor signature delta, etc.). Further, the mappings may also be derived from sources, publications, and documents that define a number of odors (e.g., butter, celery, pear, smoke, tar, and so on). The generation component 215 may map the flavor signature delta to a vector that the odor diffusing device 115 can reproduce using the odor-odor map 227. Once mapped, the generation component 215 creates a package readable by the odor diffusing device 115. The package includes the mixture of odor compounds translated from the flavor signature delta and formatted to be readable by the odor diffusing device 115. For instance, the generation component 215 may format the flavor signature delta using an API provided by the odor diffusing device 115.

In one embodiment, the communication component 220 may transmit data between various devices and servers in the computing environment 100. For example, the communication component 220 may transmit the generated package providing the flavor signature delta to the odor diffusing device 115. The communication component 220 may also issue a command to the odor diffusing device 115 to diffuse the odor compounds provided in the package.

As stated, the signature management application 107 may generate and present suggestions to a user for ingredients or additional cooking steps to perform based on missing (or inadequate) odor compounds identified in the flavor signature delta. In one embodiment, the determination component 210 is further configured to identify mappings from missing odor compounds to a particular ingredient (or cooking technique) using the odor-ingredient map 228. In one embodiment, the odor-ingredient map 228 specifies predefined mappings from odor compounds to particular ingredients or techniques. For example, assume that a given flavor signature delta indicates that the actual dish is low in estragole, a compound commonly found in tarragon. The determination component 210 may identify, using the odor-ingredient map 228, that the actual dish is lacking in tarragon. The determination component 210 may then calculate, based on the value specified in the flavor signature delta, how much of a mapped ingredient to compensate for that value. As another example, the determination component 210 may identify a given odor compound that is released from an ingredient in a recipe based on some cooking technique (e.g., the ingredient is heated to a particular temperature).

Further, the communication component 220 may send a query to the QA application 122 that includes, e.g., data included with the recipe profile 226, flavor signature data, and identified ingredients. The query sent by the signature management application 107 may include a recipe, dish name, and the identified ingredients. In turn, the QA application 122 may return a listing of recipe combinations using the identified ingredients. The determination component 210 may rank the recipe combinations based on a number of similar recipes using the ingredients, relevance measures, and the like.

In one embodiment, the generation component 215 is further configured to create suggestions from the results of the determination component 210 and the QA application 122. For example, the generation component 215 may format text output or format the suggestions in, e.g., an XML file for presentation by a web browser or productivity application.

Figure 3:
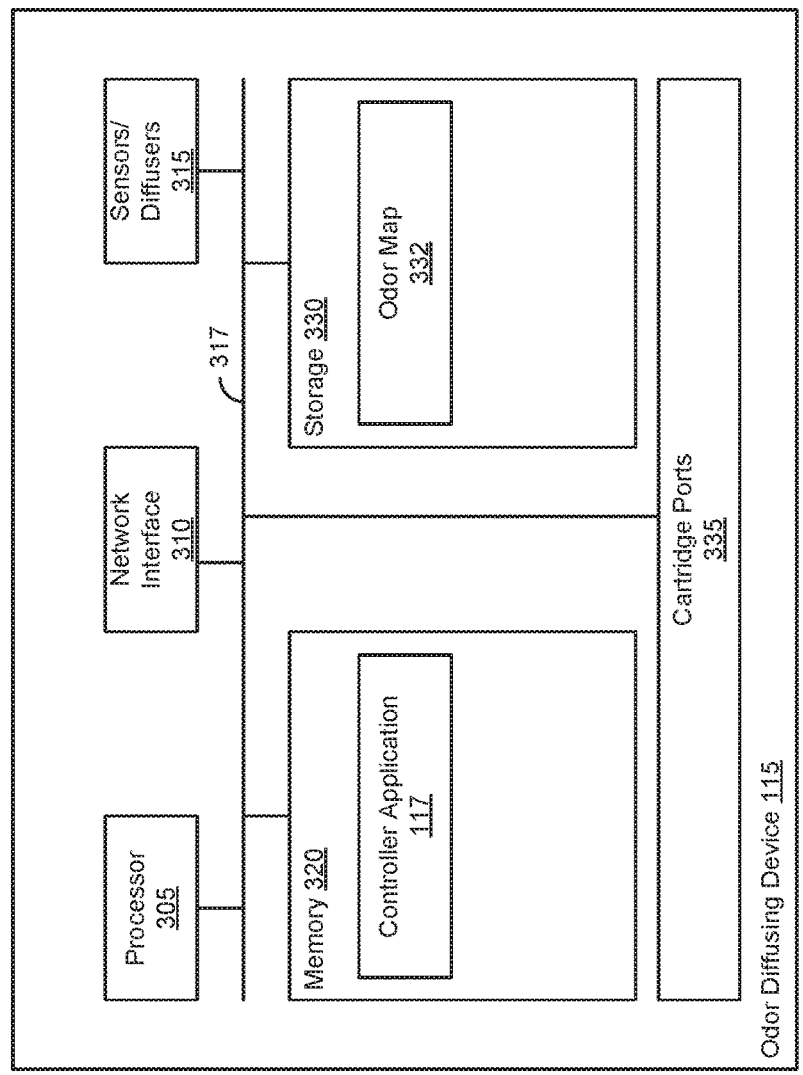
FIG. 3 further illustrates the odor diffusing device described relative to FIG. 1, according to one embodiment.

FIG. 3 further illustrates the odor diffusing device 115 described relative to FIG. 1, according to one embodiment. As shown, the odor diffusing device 115 includes a processor 305, a network interface 310, sensor/diffusers 315, a memory 320, a storage 330, and one or more odor cartridge ports 335, each interconnected via a bus 317.

The processor 305 retrieves and executes programming instructions stored in the memory 320 as well as stores and retrieves application data residing in the storage 330. The bus 317 is used to transmit programming instructions and application data between processor 305, network interface 310, storage 330, memory 320, the sensor/diffusers 315, and the odor cartridges 335. Note, the processor 305 is included to be representative of a single CPU, multiple CPUs, a single CPU having multiple processing cores, and the like. Memory 320 is generally included to be representative of a random access memory. Storage 330 may be a disk drive storage device. Although shown as a single unit, storage 330 may be a combination of fixed and/or removable storage devices, such as fixed disc drives, removable memory cards, or optical storage, network attached storage (NAS), or a storage area-network (SAN). In one embodiment, the odor cartridge ports 335 house odor cartridges that the sensor/diffusers 315 may diffuse.

Illustratively, memory 320 includes the controller application 117. And storage 330 includes an odor-map 332. The controller application 117 manages the sensor/diffusers 315, e.g., causing the diffusers to emit a mixture of the odor cartridges from the odor cartridge ports 335. In addition, the controller application 117 may receive communications from the signature management application 107, such as odor combination mixtures to via the sensor/diffusers 315.

Figure 4:
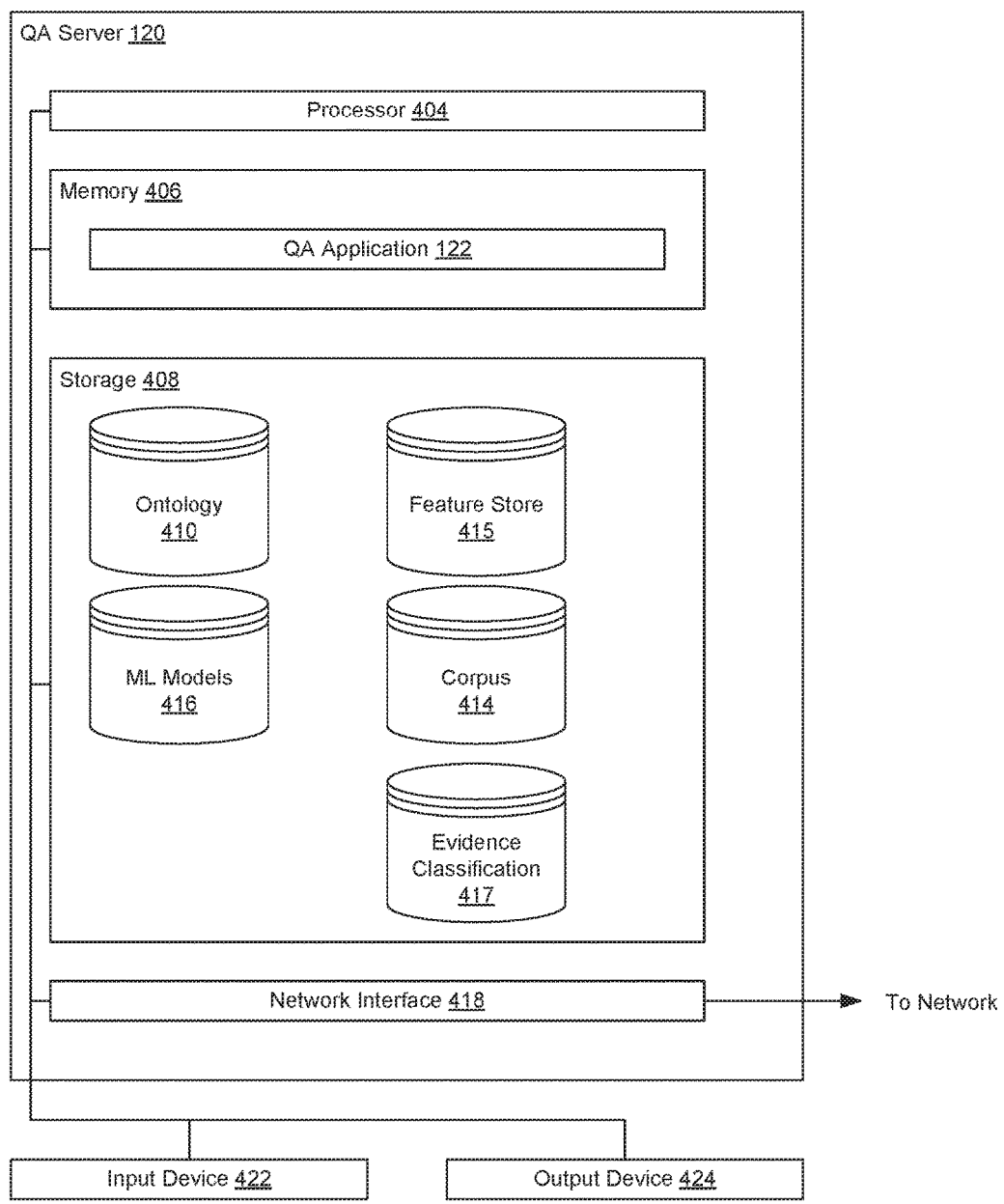
FIG. 4 further illustrates the question answering (QA) server described relative to FIG. 1, according to one embodiment.

FIG. 4 further illustrates the question answering (QA) server 120 described relative to FIG. 1, according to one embodiment. The QA server 120 generally includes a processor 404 connected via a bus to a memory 406, a network interface device 418, a storage 408, an input device 422, and an output device 424. The QA server 120 is generally under the control of an operating system. Generally, any operating system supporting the functions disclosed herein may be used. The processor 404 is included to be representative of a single CPU, multiple CPUs, a single CPU having multiple processing cores, and the like. Similarly, the memory 406 may be a random access memory. While the memory 406 is shown as a single identity, it should be understood that the memory 406 may comprise a plurality of modules, and that the memory 406 may exist at multiple levels, from high speed registers and caches to lower speed but larger DRAM chips. The network interface device 418 may be any type of network communications device allowing the QA server 120 to communicate with other computers via the network 135.

The storage 408 may be a persistent storage device. Although the storage 408 is shown as a single unit, the storage 408 may be a combination of fixed and/or removable storage devices, such as fixed disc drives, solid state drives, removable memory cards, optical storage and network storage systems.

As shown, the memory 406 contains the QA application 122, which is an application generally configured to operate a deep question answering (QA) system. One example of a deep QA system is Chef Watson, by the IBM Corporation of Armonk, N.Y. In particular, a user may submit a case (also referred to as a query) to the QA application 122, which will then provide an answer to the case based on an analysis of a corpus of information. In the present context, a case may correspond to a query including a recipe, flavor signature delta measures, and ingredients identified as missing in an actual prepared dish. The QA application 122 may execute a pipeline to generate a response to the case, which is returned to the user. In the present context, the answer may correspond to a suggestion as to an amount of the identified ingredient to add in a subsequent preparation of the recipe (or at a next stage of preparation to account for the flavor signature delta). The QA application 122 may further be configured to classify questions, identify features highly relevant to generating a correct response to the questions, and store the resulting relationships for later use.

As shown, storage 408 contains the ontology 410, corpus 414, feature store 415, ML models 416, and evidence classification 417. The ontology 410 provides a structural framework for organizing information. An ontology formally represents knowledge as a set of concepts within a domain, and the relationships between those concepts. The corpus 414 is a body of information used by the QA application 122 to generate answers to cases. For example, the corpus 414 may contain dictionary definitions and recipes obtained from various sources (e.g., recipe websites, cookbooks, recipe profiles 226, etc.). Feature store 415 stores a mapping between question context and features. If the features are not present in candidate answers for the question, processing of those candidate answers by the QA application 122 may be skipped to improve performance and efficiency. ML models 416 are models created by the QA application 122 during the training phase, which are used during a runtime pipeline to score and rank candidate answers to cases based on features previously generated for each answer. Evidence classification 417 stores relationships between evidence from the corpus 414, the question context, and the predictive features.

The input device 422 may provide a keyboard and/or a mouse, etc. The output device 424 may be any conventional display screen. Although shown separately from the input device 422, the output device 424 and input device 422 may be combined. For example, a display screen with an integrated touch-screen may be used.

Figure 5:
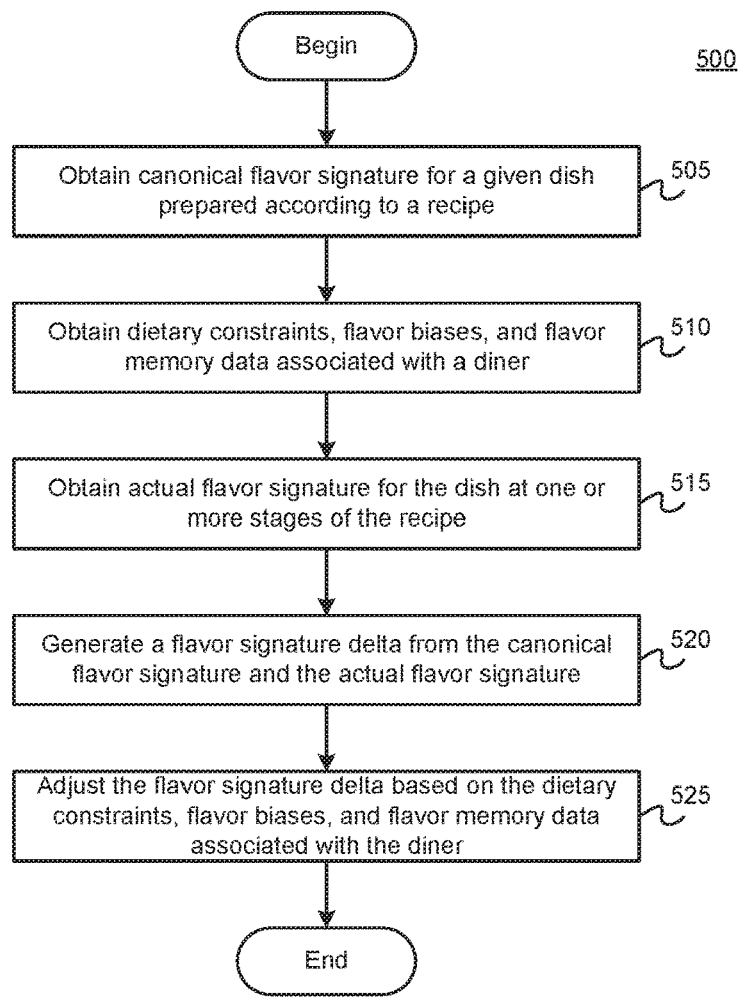
FIG. 5 illustrates a method for determining a flavor signature delta for a given dish, according to one embodiment.

FIG. 5 illustrates a method 500 for determining a flavor signature delta for a given dish, according to one embodiment. As shown, the method 500 begins at step 505, where the retrieval component 205 obtains a flavor signature for a canonical dish (i.e., a dish prepared according to a recipe, such as a recipe associated with a recipe profile 226). The canonical flavor signature may be previously stored in a data store of the computing system 105. Further, the retrieval component 205 may also obtain odor compound measurements from the odor sensing device 110 in real-time from a sample of the dish. The retrieval component 205 may then format the measurements into the flavor signature for the dish. For example, to do so, the retrieval component 205 may map each of the measurements to a particular index of a flavor signature representing a corresponding odor compound.

As stated, the dish may be prepared for a given diner (e.g., at a restaurant). At step 510, the retrieval component 205 obtains dietary constraints, flavor biases, and flavor memory data associated with the diner. For instance, the retrieval component 205 may obtain identifying information of the diner (e.g., a name, phone number, other identification number) and use the identifying information to retrieve an associated diner profile 225, which stores the dietary constraint and flavor bias and memory information.

At step 515, the retrieval component 205 obtains a flavor signature from the actual dish prepared according to the recipe. To do so, the retrieval component 205 may obtain measurements from the odor sensing device 110 in real-time from a sample of the actual dish. The retrieval component 205 may then format the measurements into the flavor signature.

At step 520, the determination component 210 generates a flavor signature delta from the flavor signature of the canonical dish and the flavor signature of the actual dish. For example, to do so, the determination component 210 may calculate a difference between the underlying sparse vectors of the flavor signatures. As stated, the flavor signature delta represents odor compounds present in the canonical dish but absent (or relatively weak) in the actual dish. In some cases, odor compounds may be present in the actual dish that are absent in the canonical dish. In such a case, the resulting flavor signature delta may have negative values in corresponding indices. In one embodiment, the determination component 210 may change such values to zero.

At step 525, the determination component 210 optionally adjusts the flavor signature delta based on the dietary constraints, flavor biases, and flavor memory data associated with the diner profile 225. For example, assume that, for a given barbecue dish, the diner has flavor memories of the dish having a smoky and sweet odor, where those odors are not as pronounced in the actual dish (as indicated by the flavor signature delta). In such a case, the determination component 210 may increase the values representing the corresponding odor compounds by a specified measure.

Figure 6:
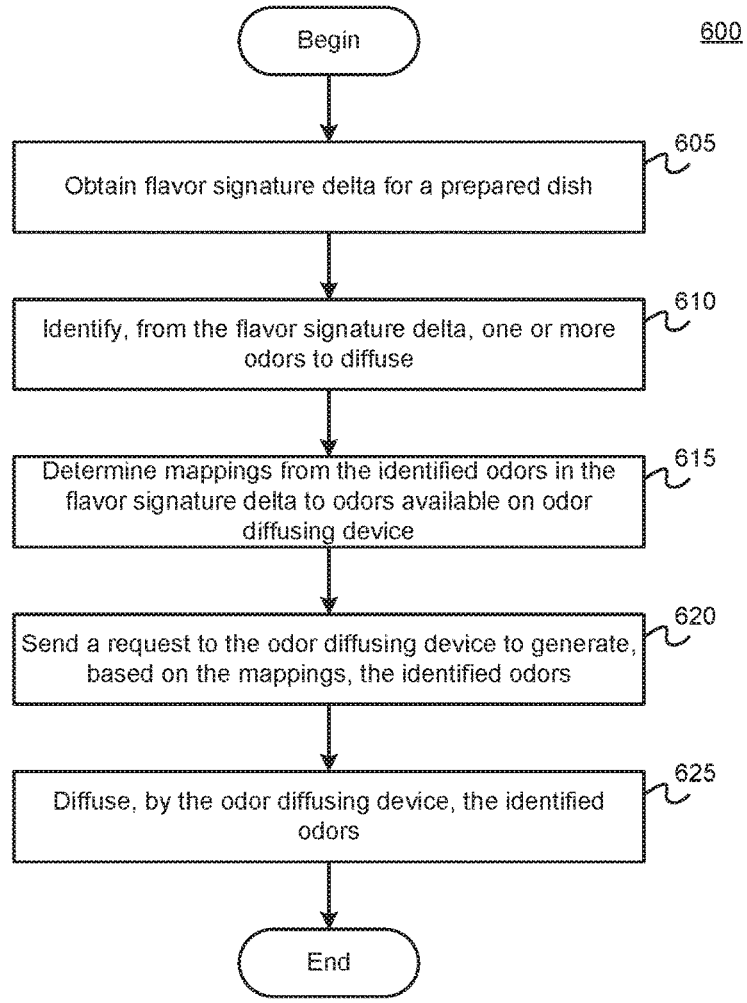
FIG. 6 illustrates a method for determining an odor mixture to diffuse based on a flavor signature delta generated for a given dish, according to one embodiment.

FIG. 6 illustrates a method 600 for determining an odor mixture to diffuse based on a flavor signature delta generated for a given dish, according to one embodiment. As shown, method 600 begins at step 605, where the determination component 210 obtains a flavor signature delta between a canonical dish and an actual dish. At step 610, the generation component 215 identifies, from the flavor signature delta one or more odors to diffuse. For example, to do so, the generation component 215 identifies mappings of odor compounds specified in the flavor signature delta to specific odor compounds. At step 615, the generation component 215 determines mappings from the identified odor compounds in the flavor signature delta to odors that can be emitted from the odor diffusing device 115. The generation component 215 may do so by evaluating the odor-odor map 227 which maps one or more odor compounds to a particular combination of odor cartridges that can represent the compounds. Once determined, the generation component 620 may create a package including the identified odor compounds to diffuse.

At step 620, the communication component 220 sends a request to the odor diffusing device to generate identified odors. To do so, the communication component 220 may send the package to the odor diffusing device 115 to be diffused. The communication component 220 may also direct the controller application 117 to emit the odor compounds once received. At step 625, the odor diffusing device, in turn, emits the identified odor compounds.

Figure 7:
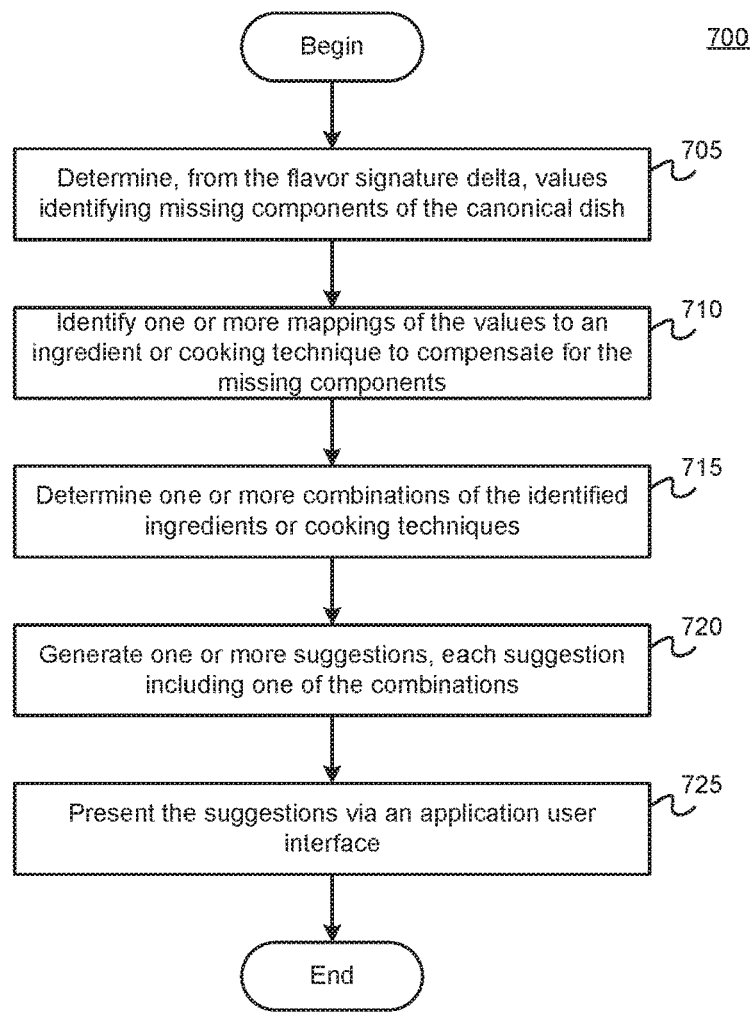
FIG. 7 illustrates a method for providing suggestions for preparing a given dish based on a flavor signature delta generated for the dish, according to one embodiment.

FIG. 7 illustrates a method 700 for providing suggestions for preparing a given dish based on a flavor signature delta generated for the dish, according to one embodiment. As shown, method 700 begins at step 705, where the determination component 705 determines, from an obtained flavor signature delta between a canonical and an actual dish, values identifying missing components of the canonical dish. Such values are generally positive values in one or more indices of the flavor signature delta, which indicate that an odor compound was present in the canonical dish but absent or comparatively weak (e.g., using a specified threshold) in the actual dish.

At step 710, the determination component 210 identifies one or more mappings of flavor signature delta values to an ingredient or cooking technique to compensate for the missing components. As stated, the determination component 210 may evaluate the values and underlying indices relative to the odor-ingredient map 228 to identify such mappings. At step 715, the determination component 210 determines one or more combinations of the identified ingredients or techniques for a given suggestion. To do so, the determination component 210 may generate a query including the identified missing components and recipe. The communication component 220 may then send the query to the QA application 122, which, in turn, returns the combinations suitable for a subsequent preparation of the recipe (or for a later stage of preparation for the recipe).

At step 720, the generation component 215 creates one or more suggestions, each suggestion including one of the combinations. The suggestions may be in a text format and stored in a data store. At step 725, the communication component 220 presents the suggestions to the user via a user interface provided by the signature management application 107. The user may view the suggestions and adjust a cooking method based on the provided suggestions.

Figure 8:
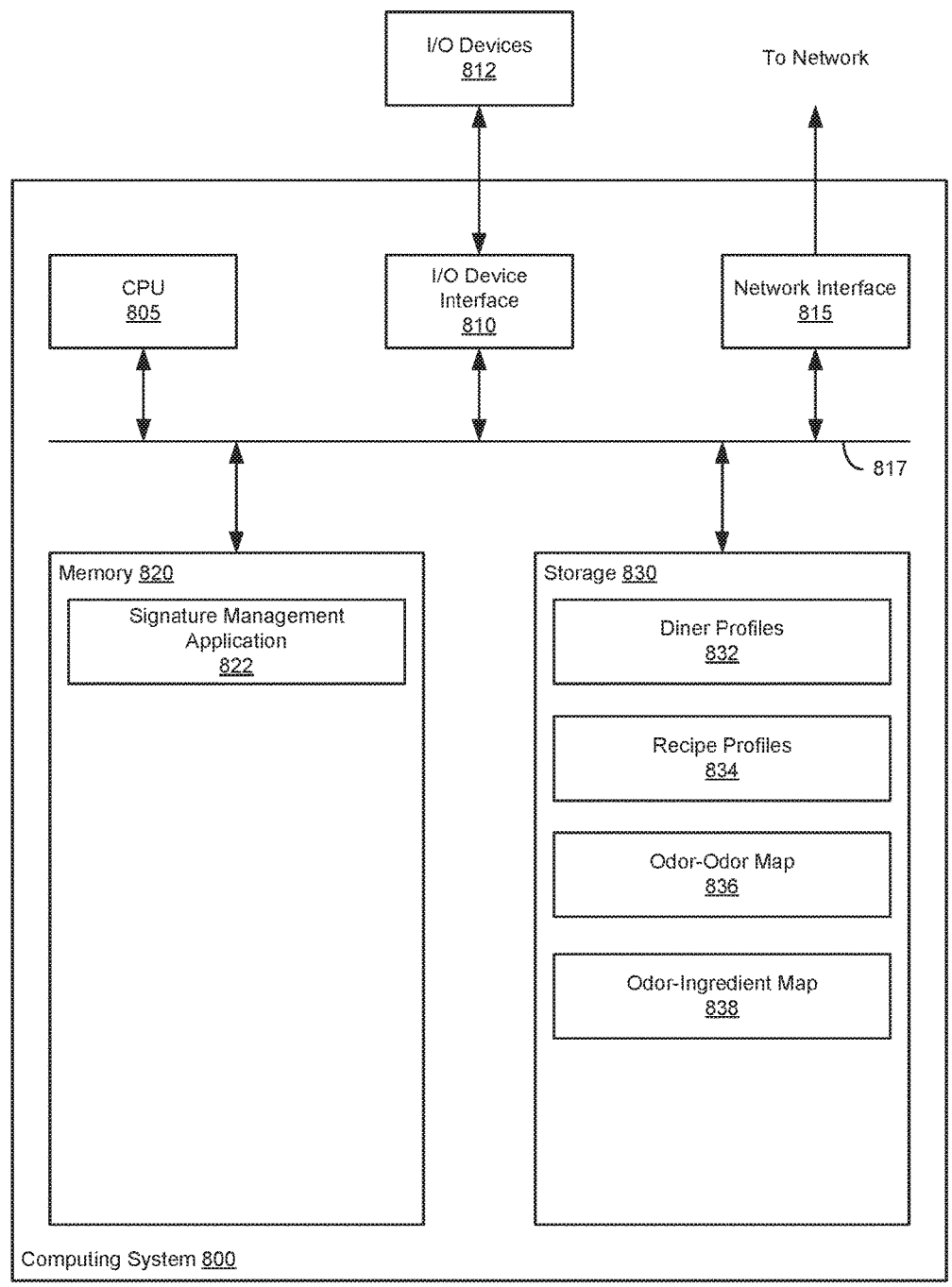
FIG. 8 illustrates an example computing system configured to generate a flavor signature delta for determining an odor mixture to diffuse and for providing suggestions for preparing the dish, according to one embodiment.

FIG. 8 illustrates an example computing system 800 configured to generate a flavor signature delta for determining an odor mixture to diffuse and for providing suggestions for preparing the dish, according to one embodiment. As shown, the computing system 800 includes, without limitation, a central processing unit (CPU) 805, a network interface 815, a memory 820, and storage 830, each connected to a bus 817. The computing system 800 may also include an I/O device interface 810 connecting I/O devices 812 (e.g., keyboard, display, mouse devices, etc.) to the computing system 800. Further, in context of the present disclosure, the computing elements shown in the computing system 800 may correspond to a physical computing system (e.g., a system in an enterprise network) or a virtual computing instance.

CPU 805 retrieves and executes programming instructions stored in memory 820 as well as stores and retrieves application data residing in the storage 830. The bus 817 is used to transmit programming instructions and application data between CPU 805, I/O devices interface 810, storage 830, network interface 815, and memory 820. Note, CPU 805 is included to be representative of a single CPU, multiple CPUs, a single CPU having multiple processing cores, and the like. Memory 820 is generally included to be representative of a random access memory. Storage 830 may be a disk drive storage device. Although shown as a single unit, storage 830 may be a combination of fixed and/or removable storage devices, such as fixed disc drives, removable memory cards, or optical storage, network attached storage (NAS), or a storage area-network (SAN).

Illustratively, memory 820 includes a signature management application 822. And storage 830 includes one or more diner profiles 832, one or more recipe profiles 834, an odor-odor-map 836, and an odor-ingredient map 838. In one embodiment, the signature management application 822 formats inputs provided by an odor sensing device (e.g., a device capable of performing GC-MS techniques) into a flavor signature providing measurements of odor compounds observed in a sample of a dish. Further, the signature management application 822 may associate a flavor signature with a given recipe profile 834.

In addition, the signature management application 822 may generate a flavor signature delta between flavor signatures between a canonical dish and an actual dish prepared according to one of the recipe profiles 834. As stated, the flavor signature delta represents a difference in odor compounds between the canonical and actual dishes. In particular, the flavor signature delta indicates a measure of odor compounds in the canonical dish over the actual dish, which represents odor compounds that are present in the canonical dish but absent (or relatively weak) in the actual dish.

In one embodiment, the signature management application 822 may identify a combination of odor compounds to emit from an odor diffusing device, based on the flavor signature delta generated for a canonical dish and an actual dish prepared according to a recipe. The signature management application 822 may do so by evaluating mappings (e.g., in the odor-odor map 836) between an odor compound identified in the flavor signature to odor compounds that can be emitted from cartridges of the odor diffusing device. The signature management application 822 may then generate an odor package readable by the odor diffusing device and a directive to emit the specified odor compounds.

In one embodiment, the signature management application 822 may generate suggestions for a user on a subsequent preparation of a dish according to a recipe (or in a subsequent stage of preparation), based on the flavor signature delta between the canonical dish and the actual dish. To do so, the signature management application 822 identifies mappings (e.g., using the odor-ingredient map 838) from a given odor compound (including the measurement specified in the corresponding index of the flavor signature delta) to a given ingredient or cooking technique that would strengthen the measure of the odor compound in the actual dish. The signature management application 107 may rank and output the suggestions based on relevance, popularity, and the like.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

In the following, reference is made to embodiments presented in this disclosure. However, the scope of the present disclosure is not limited to specific described embodiments. Instead, any combination of the following features and elements, whether related to different embodiments or not, is contemplated to implement and practice contemplated embodiments. Furthermore, although embodiments disclosed herein may achieve advantages over other possible solutions or over the prior art, whether or not a particular advantage is achieved by a given embodiment is not limiting of the scope of the present disclosure. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Aspects of the present disclosure may take the form of an entirely hardware embodiment, an entirely software embodiment (including firmware, resident software, microcode, etc.) or an embodiment combining software and hardware aspects that may all generally be referred to herein as a "circuit," "module" or "system."

Embodiments presented herein may comprise a system, a method, and/or a computer program product. The computer program product may include a computer readable storage medium (or media) having computer readable program instructions thereon for causing a processor to carry out aspects of the present disclosure.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present disclosure may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the present disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments presented herein. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Embodiments of the present disclosure may be provided to end users through a cloud computing infrastructure. Cloud computing generally refers to the provision of scalable computing resources as a service over a network. More formally, cloud computing may be defined as a computing capability that provides an abstraction between the computing resource and its underlying technical architecture (e.g., servers, storage, networks), enabling convenient, on-demand network access to a shared pool of configurable computing resources that can be rapidly provisioned and released with minimal management effort or service provider interaction. Thus, cloud computing allows a user to access virtual computing resources (e.g., storage, data, applications, and even complete virtualized computing systems) in "the cloud," without regard for the underlying physical systems (or locations of those systems) used to provide the computing resources.

Typically, cloud computing resources are provided to a user on a pay-per-use basis, where users are charged only for the computing resources actually used (e.g. an amount of storage space consumed by a user or a number of virtualized systems instantiated by the user). A user can access any of the resources that reside in the cloud at any time, and from anywhere across the Internet. In context of the present disclosure, a user may access applications (e.g., the signature management application) or related data available in the cloud. For example, the signature management application could execute on a computing system in the cloud and evaluate a flavor signature delta between flavor signatures of a canonical dish and an actual dish. In such a case, the signature management application could generate and store the flavor signature delta and store at a storage location in the cloud. Doing so allows a user to access this information from any computing system attached to a network connected to the cloud (e.g., the Internet).

While the foregoing is directed to embodiments of the present disclosure, other and further embodiments may be devised without departing from the basic scope thereof, and the scope thereof is determined by the claims that follow.

What is claimed is:

1. A method comprising:
obtaining a first flavor signature for a first sample, wherein the first flavor signature includes a vector indicating a respective measure for each respective olfactory compound of a plurality of olfactory compounds that are present in the first sample;

obtaining a second flavor signature for a second sample, wherein the second flavor signature provides a vector indicating a respective measure for each respective olfactory compound of the plurality of olfactory compounds that are present in the second sample;

generating a flavor signature delta from the first and second flavor signatures, wherein the flavor signature delta indicates, for each respective olfactory compound of the plurality of olfactory compounds, a respective difference between the respective measure of the respective olfactory compound in the first sample and the respective measure of the respective olfactory compound in the second sample;

identifying, by operation of one or more computer processors, one or more ingredients that are not present in the second sample and are present in the first sample, wherein each of the one or more ingredients are identified based on at least one of the differences indicated in the flavor signature delta;

identifying, by operation of one or more computer processors, one or more preparation techniques that were used to prepare the first sample and were not used to prepare the second sample, wherein the one or more preparation techniques are identified based on at least one of the differences indicated in the flavor signature delta; and generating one or more suggestions for preparing a third sample, wherein the one or more suggestions include an indication of the one or more identified ingredients and the one or more identified preparation techniques.

2. The method of claim 1, wherein identifying the one or more ingredients comprises:
obtaining, for one or more of the differences in the flavor signature delta, a mapping to an ingredient.

3. The method of claim 1, wherein the one or more preparation techniques include an indication that the second sample should be cooked for a longer period of time.

4. The method of claim 1, wherein the first sample represents a canonical version of a dish prepared according to a recipe and wherein the second sample represents a version of the dish prepared subsequent to the first sample.

5. The method of claim 1, wherein the first flavor signature, second flavor signature, and flavor signature delta are sparse vectors.

6. The method of claim 1, wherein the first flavor signature and the second flavor signature are obtained from an olfactory sensor device.

7. The method of claim 1, wherein the at least the second flavor signature is captured at one or more stages of preparation of the second sample.

8. A computer program product, comprising:
a computer-readable storage medium storing instructions, which, when executed on a processor, performs an operation, comprising:
obtaining a first flavor signature for a first sample, wherein the first flavor signature includes a vector indicating a respective measure for each respective olfactory compound of a plurality of olfactory compounds that are present in the first sample;
obtaining a second flavor signature for a second sample, wherein second flavor signature provides a vector indicating a respective measure for each respective olfactory compound of the plurality of olfactory compounds that are present in the second sample;
generating a flavor signature delta from the first and second flavor signatures, wherein the flavor signature delta indicates, for each respective olfactory compound of the plurality of olfactory compounds, a respective difference between the respective measure of the respective olfactory compound in the first sample and the respective measure of the respective olfactory compound in the second sample;
identifying one or more ingredients that are not present in the second sample and are present in the first sample, wherein each of the one or more ingredients are identified based on at least one of the differences indicated in the flavor signature delta;
identifying, one or more preparation techniques that were used to prepare the first sample and were not used to prepare the second sample, wherein the one or more preparation techniques are identified based on at least one of the differences indicated in the flavor signature delta; and
generating one or more suggestions for preparing a third sample, wherein the one or more suggestions include an indication of the one or more identified ingredients and the one or more identified preparation techniques.

9. The computer program product of claim 8, wherein identifying the one or more ingredients comprises:
obtaining, for one or more of the differences in the flavor signature delta, a mapping to an ingredient.

10. The computer program product of claim 8, wherein the one or more preparation techniques include an indication that the second sample should be cooked for a longer period of time.

11. The computer program product of claim 8, wherein the first sample represents a canonical version of a dish prepared according to a recipe and wherein the second sample represents a version of the dish prepared subsequent to the first sample.

12. The computer program product of claim 8, wherein the first flavor signature, second flavor signature, and flavor signature delta are sparse vectors.

13. The computer program product of claim 8, wherein the first flavor signature and the second flavor signature are obtained from an olfactory sensor device.

14. The computer program product of claim 8, wherein the at least the second flavor signature is captured at one or more stages of preparation of the second sample.

15. A system, comprising:
a processor; and
a memory storing program code, which, when executed on the processor, performs an operation, comprising:
obtaining a first flavor signature for a first sample, wherein the first flavor signature includes a vector indicating a respective measure for each respective olfactory compound of a plurality of olfactory compounds that are present in the first sample;
obtaining a second flavor signature for a second sample, wherein second flavor signature provides a vector indicating a respective measure for each respective olfactory compound of the plurality of olfactory compounds that are present in the second sample;
generating a flavor signature delta from the first and second flavor signatures, wherein the flavor signature delta indicates, for each respective olfactory compound of the plurality of olfactory compounds, a respective difference between the respective measure of the respective olfactory compound in the first sample and the respective measure of the respective olfactory compound in the second sample;

identifying one or more ingredients that are not present in the second sample and are present in the first sample, wherein each of the one or more ingredients are identified based on at least one of the differences indicated in the flavor signature delta; and generating one or more suggestions for preparing a third sample, wherein the one or more suggestions include an indication of the one or more identified ingredients and the one or more identified preparation techniques.

16. The system of claim 15, wherein identifying the one or more ingredients comprises:

obtaining, for one or more of the differences in the flavor signature delta, a mapping to an ingredient.

17. The system of claim 15, wherein the one or more preparation techniques include an indication that the second sample should be cooked for a longer period of time.

18. The system of claim 15, wherein the first sample represents a canonical version of a dish prepared according to a recipe and wherein the second sample represents a version of the dish prepared subsequent to the first sample.

19. The system of claim 15, wherein the first flavor signature, second flavor signature, and flavor signature delta are sparse vectors.

20. The system of claim 15, wherein the at least the second flavor signature is captured at one or more stages of preparation of the second sample.

* * * * *